United States Patent [19]

Drouin et al.

[11] 4,389,913
[45] Jun. 28, 1983

[54] SCREW EXTRACTOR

[76] Inventors: Gilbert Drouin, 47 St. Andre, St-Luc, Quebec, Canada, JOJ 2AO; Jean Lacoste, 1530 Ouest Bl. Dernard, Apt. 14, Outremont, Quebec, Canada, H2V 1W8; Gilles Tremblay, 354 Redfern, Westmount, Quebec, Canada, H3Z 2G5

[21] Appl. No.: 239,987

[22] Filed: Mar. 3, 1981

[51] Int. Cl.³ ............................................. B25B 13/50
[52] U.S. Cl. ...................................... 81/53.2; 279/42; 408/173
[58] Field of Search ........................... 81/53.2; 279/42; 408/173, 161, 163; 7/158

[56] References Cited

U.S. PATENT DOCUMENTS

| 192,423 | 6/1877 | Elterich | 279/42 |
| 1,548,835 | 8/1925 | French | 81/53.2 |
| 1,683,796 | 9/1928 | Pearce | 81/53.2 |
| 1,848,590 | 3/1932 | Willis | 81/53.2 |
| 3,735,650 | 5/1973 | Weng, Jr. | 81/53.2 |
| 4,204,308 | 5/1980 | Marling | 81/53.2 |

FOREIGN PATENT DOCUMENTS 611906  7/1926  France ...................... 81/53.2

Primary Examiner—James L. Jones, Jr.
Attorney, Agent, or Firm—Watson, Cole, Grindle & Watson

[57] ABSTRACT

A tool for use in removing broken or inoperative screw fasteners. The tool has a tubular-shaped extension at one end with cutting teeth projecting axially from the extension. The teeth can cut around a fastener when the tool is rotated in one direction to provide a stub end on the fastener over which the extension fits. The extension is then tightened on the stub end and teeth, extending radially inwardly from the extension, tightly grip the stub end so that the fastener can be unscrewed on reverse rotation of the tool.

3 Claims, 7 Drawing Figures

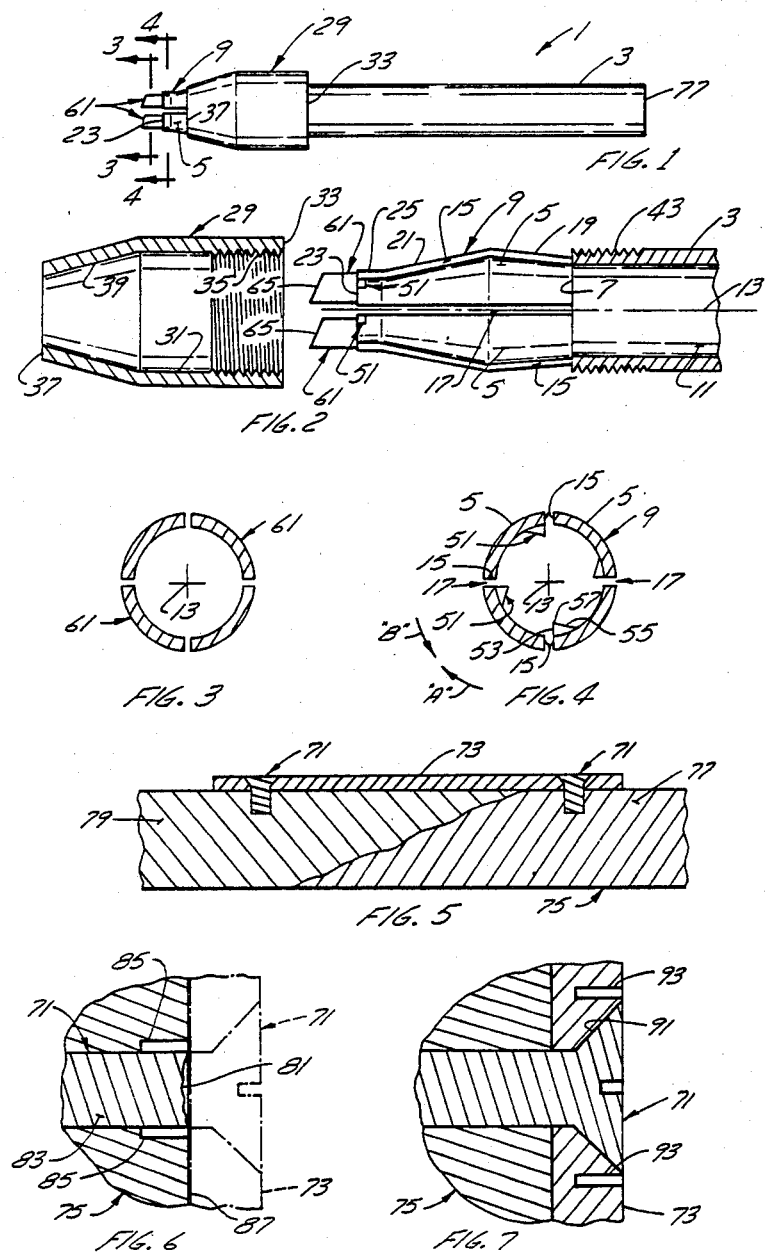

SCREW EXTRACTOR

This invention is directed toward a tool for use in removing broken or misshapen fasteners, particularly broken or misshapen screw fasteners.

Screw fasteners are often employed in surgery to connect or join broken or cracked bones. Once the bones have healed, the screws are usually removed. Occasionally, however, the head of the screw breaks off, or becomes misshapen, during removal attempts. The broken or inoperative screw must then be removed with pliers, or by another difficult and time comsuming removal methods.

It is the purpose of the present invention to provide a tool which can be used to easily and quickly remove a broken or misshapen screw fastener in one simple operation.

In accordance with the present invention, there is provided a tool having means for cutting a portion of the bone immediately adjacent the fastener, when the tool is rotated and advanced. The bone is cut away sufficiently to expose an end of the fastener which can be gripped by the tool. After sufficient material has been cut away, rotation and advancement of the tool is halted with the tool now encircling the exposed end of the fastener. The tool is now operated to grip the exposed end of the fastener and the tool is then rotated in a reverse direction to withdraw the fastener from the bone.

From the above it will be seen that a single tool in a simple cutting, locking and withdrawing sequence can be used to remove damaged and/or broken fasteners.

The invention is particularly directed toward a tool for use in extracting a broken fastener, the tool having a main body and a tubular-shaped extension projecting from one end of the body. Cutting means project axially from the free end of the extension and gripping means project radially inwardly from the extension. Means are provided to reduce the size of the free end of the extension to move the gripping means radially inwardly.

The invention will now be described in detail having reference to the accompanying drawings in which:

FIG. 1 is a side view of the tool;

FIG. 2 is a detail, longitudinal cross-section view of the tool parts;

FIG. 3 is a cross-section view of the cutting teeth taken along line 3—3 of FIG. 1;

FIG. 4 is a cross-section view of the fingers taken along line 4—4 of FIG. 1;

FIG. 5 is a cross-section view showing a bone plate fastened to a bone;

FIG. 6 is a cross-section view of a fastener with a broken head; and

FIG. 7 is a cross-section view of a fastener with a deformed head.

The tool 1 of the present invention has a tubular, preferably cylindrical, body 3. A set of flexible fingers 5 project from one end 7 of the body 3 to form a tubular-shaped extension 9 to the body 3. Four fingers 5 can be provided to form the extension 9, the fingers 5 either formed integrally with body 3 as shown, or fastened to the inside surface 11 of the cylindrical body 3. Each finger 5 is curved through almost ninety degrees about the longitudinal axis 13 of the body 3 as seen in FIG. 4, to provide a generally cylindrical extension. The side edges 15 of the fingers 5 are spaced apart slightly from each other to provide a gap 17 between adjacent fingers. The outer surface of the extension 9 defined by the fingers 5 has a first inner portion 19 adjacent the body 3 that tapers slightly outwardly, a second central portion 21 that tapers slightly inwardly toward the outer ends 23 of the fingers 5, and short, third, outer cylindrical section 25 adjacent the outer ends.

Means are provided on the tool for moving the outer ends 23 of the fingers 5 toward the longitudinal axis 13 so as to reduce the diameter of the circle defined by the ends 23. These means comprise a collar or collet 29. The inner surface of the collet 29 as shown in FIG. 2 is cylindrical as shown at 31 adjacent the inner end 33 of the collet. A threaded portion 35 is provided on the cylindrical surface 31. The inner surface of the collet adjacent its outer end 37 is tapered inwardly toward the outer end 37 as shown at 39. The taper of surface 39 generally matches the taper of the central, outer surface, portion 21 of the flexible fingers 5.

The outer surface of the cylindrical body 3 is threaded, as shown at 43, adjacent the one end 7. The collet 29 is sized to slip over the fingers 5 and onto the body 3 of the tool at the one end 7, its inner threaded portion 35 engaging the outer threaded portion 43 on the tool body 3. When its threaded portion 35 initially engages the threaded portion 43 on the tool body 3, the inner tapered surface 39 closely overlies the tapered central portion 21 of the fingers 5. As the collet 29 is threaded onto the body 3, moving axially away from the outer ends 23 of the fingers 5, its tapered surface 39 bears against the tapered surface 21 of the fingers 5, pushing them radially inwardly so as to reduce the diameter of the circle defined by the finger ends 23.

The tool construction defined above is well known as a simple chuck and collet arrangement for gripping other tools such as drills. In accordance with the present invention, features are added to the tool to particularly adapt it to be used in the removal of broken fasteners. To this end, gripping teeth 51 are provided on the inner surface of the gripping fingers 5 adjacent their outer ends 23. Preferably one tooth 51 is provided on each finger 5 adjacent its outer end 23. Although it can be located anywhere along the inner surface of the gripping finger 5 adjacent its outer end 23, the single tooth is preferably provided adjacent a side edge 15 of the Finger 5. Each tooth 51 is designed to grip more tightly when the tool 1 is rotated in a counterclockwise or unscrewing direction as shown in arrow "A" than when rotated in a clockwise direction as shown by arrow "B." To this end, as shown in FIG. 4, each tooth 51 has a generally radial face 53 on its counter-clockwise side, and a nearly tangential face 55 extending in a clockwise direction away from the radial face 53. The two faces 53,55 meet to define a sharp biting point 57 projecting inwardly from the finger and preferably radially aligned with an edge 15 of the finger.

While the tool has been shown and described with teeth 51 which grip more tightly in the counter-clockwise direction of rotation of the tool than in the clockwise direction, the tool can also be provided with the teeth 51 designed to grip more tightly in the clockwise direction than in the counter-clockwise direction if desired.

Cutting teeth 61 are also provided on the fingers 5. Preferably, one such tooth 61 is provided on each finger 5, projecting axially outwardly from the outer end 23 of the finger. Each cutting tooth 61 is curved through almost ninety degrees, similarly to its supporting finger 5, about the longitudinal axis 13 of the tool 1. The teeth 61 can be formed integrally with the fingers 5 as by machining for example, alternatively, the teeth 61 can be made separately from the fingers 5 and then attached, at their inner ends by welding or other suitable means, to the outer ends 23 of the fingers 5. The outer end 65 of the tooth is angled and sharpened to provide a cutting edge. The cutting teeth 61 are slightly spaced apart from each other, and are arranged in a circle about the longitudinal axis 13 of the tool.

The tool is used to remove fasteners 71 which break or deform during normal attempts to remove the fastener. Headed screw fasteners 71 as shown in FIG. 5 are often used to temporarily fasten a bone plate 73 along a cracked or broken bone 75 to hole the pieces 77, 79 of bone together while they heal. After the bone has healed it is desirable to remove the bone plate 73. The fasteners 71 however occasionally break during removal. The break 81 often occurs at the surface of the bone, and the present tool is used to remove that portion 83 of the fastener 71 which remains in the bone after the fastener has broken and the plate is removed. The tool 1 is hand-held by its body 3 and is rotated and advanced to drill a counterbore hole 85, as shown in FIG. 6, about the embedded portion 83 of the fastener, inwardly from the surface 87 of the bone. At this time the collet 29 is loose to allow the flexible fingers 5 to pass over the fastener portion 83. Once the gripping teeth 51 of the tool have passed onto the portion 83, the collet 29 is tightened to push the fingers 5 inwardly and to press the points 57 of the gripping teeth 51 into the fastener portion 83 adjacent its broken end 81. The rotation of the tool is now reversed to have the teeth 51 tightly grip the fastener portion 83 and to unscrew it out of the bone 75.

The head 91 of the fastener 71 can also become deformed during attempts to remove the bone plate 73. In this case, a larger tool 1 is employed to remove the deformed screw. The larger tool 1 has an extension 9 with an inner diameter large enough to just pass over the head 91 of the fastener 71 as the tool is hand-operated to drill a counterbore hole 93 in the plate 73 about the head 91 as shown in FIG. 7. The teeth 51 on the fingers 5 just pass over the head 91 with the collet 29 loosened. Once the teeth 51 can grip the head 91, the collet 29 is tightened and rotation of the tool is reversed to withdraw the fastener 71 out of the bone 75 and the bone plate 73.

While the tool 1 has been described with removing broken or deformed fasteners from bones and/or bone plates, the tool can be used to remove broken or deformed fasteners from other structures and/or materials as well.

We claim:

1. A tool for use in extracting a broken fastener, the tool comprising a main body, a tubular-shaped extension comprised of a plurality of slightly spaced apart, flexible curved fingers projecting from one end of the body, size-reducing means for radially reducing the size of a free end of the fingers, cutting means projecting axially from said free end of the fingers, said cutting means being radially movable by action of said size-reducing means such that said cutting means can be sized to cut around the broken fastener, gripping means comprising a plurality of teeth extending inwardly from said fingers, said gripping means being radially movable to grip the broken fastener subsequent to operation of said cutting means, each of said teeth having one side extending radially and the other side extending generally tangentially so as to securely grip the broken fastener upon a slight rotation of the body, the tangential side leading when the tool is rotated in the direction in which the fastener was rotated to fasten.

2. The tool of claim 1 wherein the cylindrical shaped extension comprises four slightly spaced apart flexible curved fingers.

3. The tool of claim 2 wherein the size reducing means comprises a collar mounted on the body, the collar axially movable along the body and having a portion partially overlying the fingers to move the fingers radially inwardly as the collar is moved axially along the body away from the free end of the fingers.

* * * * *